United States Patent
Kaushal

(10) Patent No.: US 7,579,592 B2
(45) Date of Patent: Aug. 25, 2009

(54) ILLUMINATION AND IMAGING DEVICES AND METHODS

(75) Inventor: Tej Kaushal, Malvern (GB)

(73) Assignee: QinetiQ Limited, Farnborough, Hants (GB)

(*) Notice: Subject to any disclaimer, the term of this patent is extended or adjusted under 35 U.S.C. 154(b) by 1407 days.

(21) Appl. No.: 10/204,856

(22) PCT Filed: Feb. 23, 2001

(86) PCT No.: PCT/GB01/00772
§ 371 (c)(1),
(2), (4) Date: Sep. 10, 2002

(87) PCT Pub. No.: WO01/63335
PCT Pub. Date: Aug. 30, 2001

(65) Prior Publication Data
US 2003/0047683 A1    Mar. 13, 2003

(30) Foreign Application Priority Data
Feb. 25, 2000    (GB) .............................. 0004351.3

(51) Int. Cl.
*G02B 23/12* (2006.01)
(52) U.S. Cl. .................................. 250/330; 359/291
(58) Field of Classification Search ................ 250/330; 359/291
See application file for complete search history.

(56) References Cited

U.S. PATENT DOCUMENTS

| 4,591,918 A | 5/1986 | Hisano |
| 5,023,709 A | 6/1991 | Kuwashima et al. |
| 5,660,454 A * | 8/1997 | Mori et al. .................. 362/466 |
| 5,828,485 A | 10/1998 | Hewlett |
| 5,969,754 A | 10/1999 | Zeman |

FOREIGN PATENT DOCUMENTS

| EP | 0 814 344 A | 12/1997 |
| GB | 2 218 506 A | 11/1999 |
| WO | EO 98/26583 | 6/1998 |

* cited by examiner

*Primary Examiner*—David P Porta
*Assistant Examiner*—Shun Lee
(74) *Attorney, Agent, or Firm*—Nixon & Vanderhye P.C.

(57) ABSTRACT

A thermal torch (12) comprises an infrared camera (22) and a visible light emitter (28, 26) arranged so as to illuminate hot objects with visible light. This projection of visible light onto the scene, rather than observing it at infrared wavelengths converted to visible light by a display screen, makes viewing the scene more natural. Applications include medical imaging equipment, night driving systems, stage lights, and security lights. The profile of the beam of visible light can be modulated with a beam profiler (26) which may be a LCD. The infrared camera (22) and visible projector (28,26) may be bore-sighted to facilitate overlying of the visible projected image onto the scene.

13 Claims, 7 Drawing Sheets

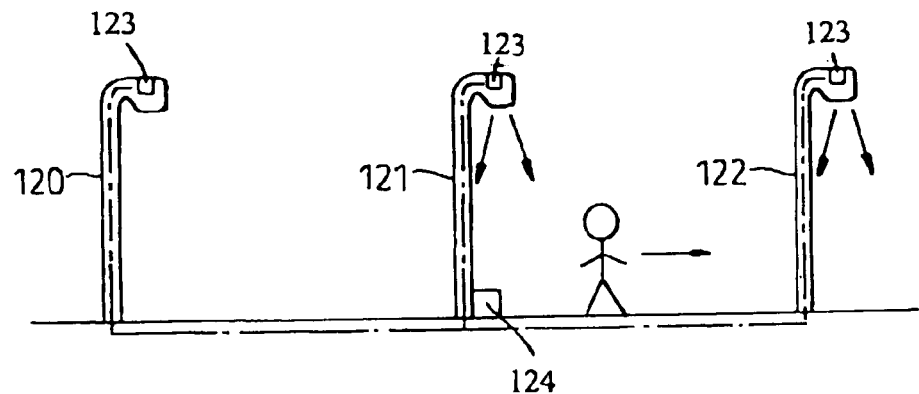
*Fig. 12A*
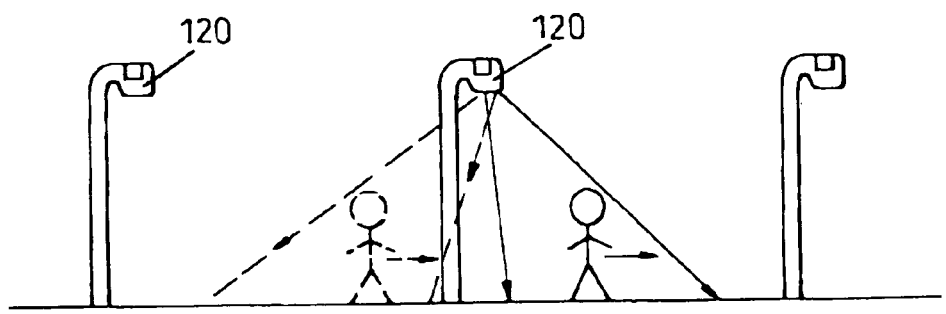
*Fig. 12B*
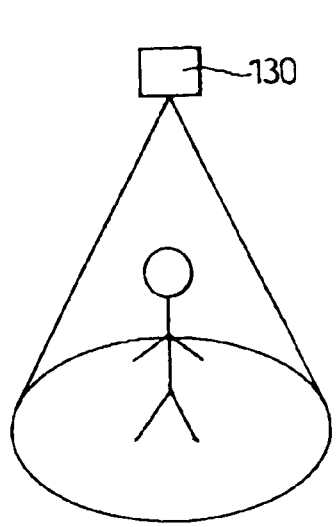
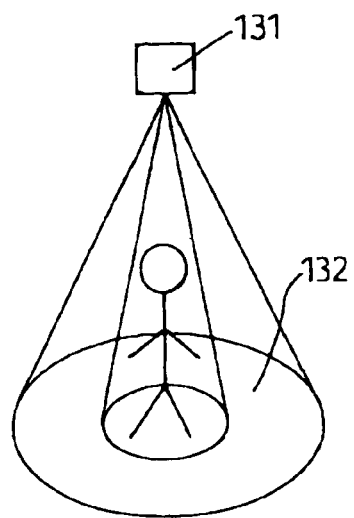
*Fig. 13A*          *Fig. 13B*

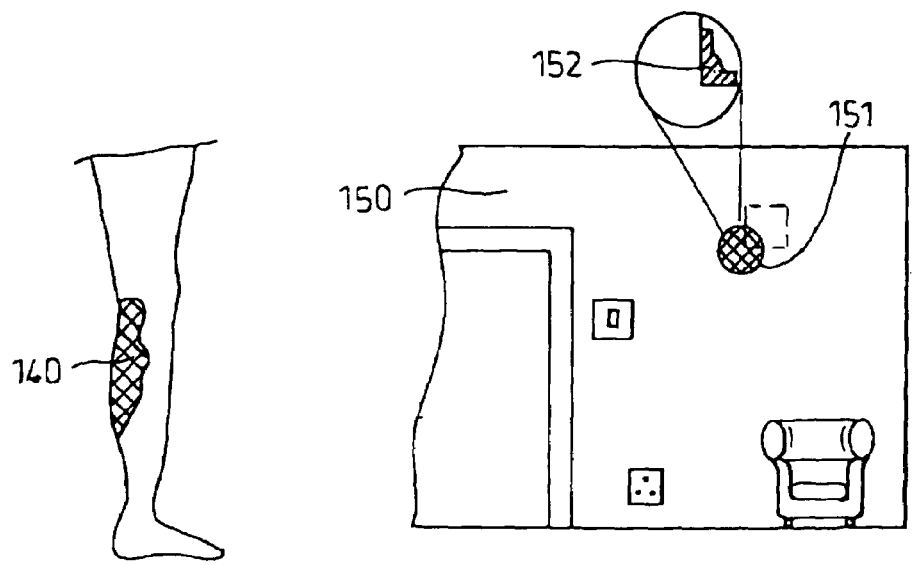
Fig. 14  Fig. 15
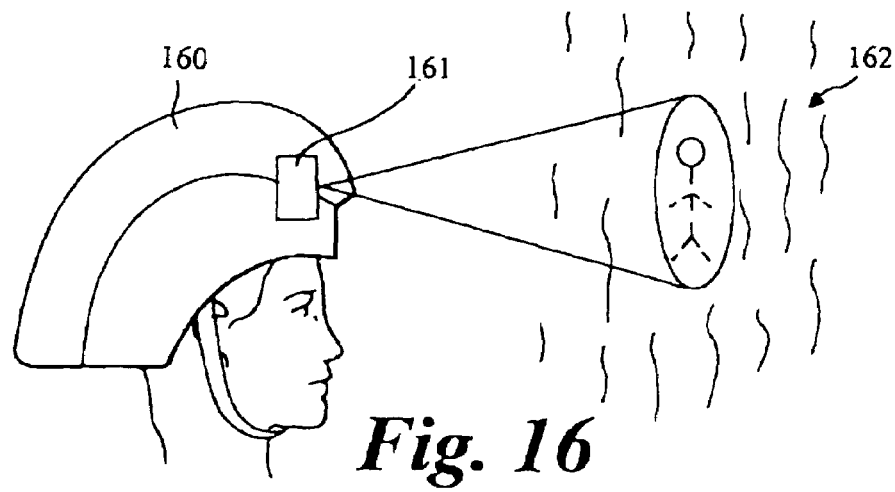
Fig. 16
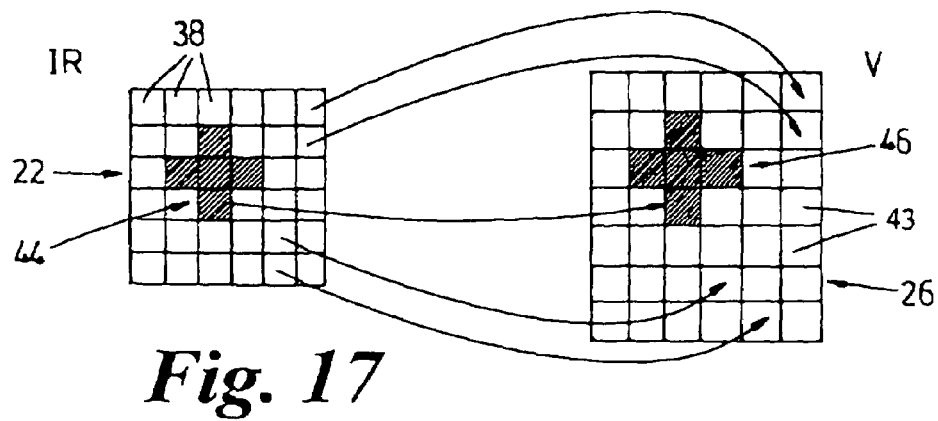
Fig. 17

ILLUMINATION AND IMAGING DEVICES AND METHODS

This application is the U.S. national phase of international application PCT/GB01/00772 filed 23 Feb. 2001, which designated the U.S.

BACKGROUND OF THE INVENTION

1. Field of the Invention

This invention relates to illuminating an observed scene with electromagnetic radiation, and to imaging. It is especially, but not exclusively, concerned with projecting light in a predetermined controlled beam, and has especial, but not exclusive, applications in thermal imaging.

The invention arose in the field of thermal imaging and will be described in relation to that, but as will be appreciated it has wider applications.

2. Discussion of Prior Art

Infra thermal imagers exist and work well. To obtain good resolution pictures, for example 512×512 pixels, it is necessary to use expensive infrared cameras which now cost around £10,000 each. This limits areas where it is practical to use thermal imaging cameras.

It is an aim of at least one aspect of the invention to attempt to reduce significantly the cost of practically useful infrared (I.R.) detector arrays.

Another problem with existing thermal imaging cameras is that it can be difficult for a user to register the thermal image presented to them on a imager display (often ghostly green) and the real visible word that they can see with their normal eyesight. One example of the is that some commercial automobiles now have an infrared night driving system which has an I.R. thermal camera with good (e.g. 512×512 pixel) resolution sending signals to a visible light projector which projects a visible light representation of the I.R. scene image into a head-up display. The head up display is typically about 10 cm×10 cm and although the windscreen of the automobile is about 200 cm×50 cm some drivers have a disturbing tendency when using the I.R. imaging system to look only through the small area of the head-up display: they may not scan the full view that they can see out of the windscreen properly at night and are psychologically reduced to driving using the head-up display alone (although they are, of course, free to look beyond it if they can discipline themselves to do so). Whilst the visible representative of the I.R. image is registered on the head-up display with the visible images seen through the windscreen, the user can still have difficulties. It is an aim of one embodiment of the invention to make driving at night using an infrared system a more natural/normal experience for the driver.

Another problem is when using infrared cameras for medical imaging (for example to find veins, hot or cold spots indicative of infection or circulation problems, or to locate burns), the user (e.g. doctor or nurse) uses an infrared imager to obtain a visible light picture on an electronic display derived from I.R. information, and then may use their skill and judgement to translate that I.R. to visible light image into movements of their hands to treat the right areas of a patient's body.

It is known for a medical I.R. imager to have an I.R. camera and a visible camera and to take both an I.R. picture and a visible light picture of part of a patient and to present the user with a combined picture on an electronic display.

SUMMARY OF THE INVENTION

It is an aim of some embodiments of the invention to facilitate a user registering infrared information with the natural view that they see in the visible spectrum with their eyes.

According to a first aspect invention comprises a projector device comprising: a detector adapted to detect radiation of a first wavelength incident upon the device from a direction; an emitter adapted to emit a beam of radiation of a second, different, wavelength; and emitted beam control means adapted to control the direction of the emitted beam to direct it in substantially the same direction as that from which came the detected radiation of the first wavelength.

It will be appreciated that the radiation of the first wavelength incident upon the detector is not radiation that has been emitted by the device: it is radiation that is emitted by an object in the observed scene and passively detected.

Thus an object emitting radiation at one wavelength can be illuminated with radiation of another wavelength by the device. For example an infrared detector may provide signals which control the emitting of a beam of visible light.

Since making the invention some prior art has been discovered. WO98/26583 relates to a medical specialist system for use in a darkened room environment to assist people who have reduced vision due to degeneration of their retina. It discloses a contrast enhancing system which emits infrared light from the system, detects infrared light reflected back off objects in a field of view, and then projects visible light into the scene so as to project a lot of visible light onto areas which have reflected a high level of the I.R. light emitted by the system, and less visible light onto those areas which reflect less back.

It is concerned with the reflectivity of objects of I.R. emitted by the system, not thermal IR actively emitted by scene objects and passively detected by an IR detector.

GB 2 218 506 discloses a lamp which emits IR radiation and detects reflected IR radiation from a person at night and turns itself on to emit visible light.

U.S. Pat. No. 5,023,709 also discloses a lamp, an automated stage lighting system, which emits IR light and detects its reflection from an I.R. reflector placed on an object or actor that the visible lamp is to track on stage.

JP 08292774 discloses controlling a visible band spot light to direct it onto a karaoke singer by using IR emitters which emit IR light and detect its reflection.

JP 08122865 discloses a camera with an IR emitter which emits an IR beam and detects its reflection from an object in a scene, and then directs its visible light flash in the direction of the IR-reflecting object.

The device may have a detection aperture, which may comprise an imaging aperture, the detector being an imaging detector. The device may be adapted to detect the direction of incidence of detected radiation and to direct the emitted beam in that direction. The structure of the device may be such that an incident beam of first wavelength radiation is detected and an emitted beam of second wavelength radiation is automatically emitted in the direction from which came the incident beam: the structure of the device may automatically align the emitted beam with a detected beam.

The detector may be adapted to detect the cross-sectional profile, or image, of an incident detected beam. The emitter may be adapted to emit an emitted beam with a variable cross-sectional profile, which may be modulated to match the profile of the detected beam.

Preferably the device has a controller adapted to control the emitter to emit radiation of the second wavelength upon detection of radiation of the first wavelength. Alternatively the emitter may emit radiation of the second wavelength when the radiation of the first wavelength is not being detected. For example the emitter may emit radiation to the profile and direction of the last detected first radiation signal or image, or it may emit radiation to a predetermined direction and/or pattern.

In some embodiments the emitter direction control means has no moving mechanical parts. Preferably the emitter beam control means is an arrangement of the optics of the device such that the detector in use detects radiation from a detection direction and the emitter emits radiation back along the detection direction. The emitter and detector are preferably boresighted to the same detection/emitting direction.

Preferably an optical alignment element is provided to register the emitted beam with the detected beam. The alignment element is preferably at least partially reflective to radiation of one of the first and second wavelengths and at least partially transmissive to radiation of the other of the first and second wavelengths. Preferably the alignment element comprises a beam splitter.

Preferably the detector comprises an imager adapted to generate first wavelength image signals representative of a scene viewed at the first wavelength. Preferably the emitter has an image emitter adapted in use to emit an image at the second wavelength. Preferably the emitted image is emitted in a direction controlled by the emitter direction control means. Preferably the emitted image substantially comprises a mapping of the detected image, having substantially the same shape and/or pattern.

The detector may comprise an imager adapted to generate first wavelength image signals representative of a scene viewed at the first wavelength, and the emitter comprises a beam profiler adapted in use to emit an image at the second wavelength, and in which the emitted image substantially comprises a mapping of the detected image, having substantially the same shape and/or pattern, the device being adapted in use to overlay the emitted image onto the scene being observed registered over the source of the detected image.

Preferably the device has first and second wavelength registration means adapted to overlay the emitted image in radiation of the second wavelength onto the observed scene so that it overlays the image detected at the first wavelength.

It will be appreciated that unless the radiation of the second wavelength emitted by the emitter travels along substantially the same path as the detected first wavelength (bore-sighted) the detected image and emitted image will register only at a predetermined distance from the device.

Preferably the beam control means comprises a spatial light modulator (SLM). The SLM may comprise a liquid crystal display adapted selectively to transmit or reflect second wavelength radiation at a plurality of regions across its effective area.

Preferably the SLM is adapted simultaneously to interact with radiation at a first region in a first way and to interact with radiation at a second region in a second, different, way so as to provide a differentiated transmission, absorption, or reflection performance at different regions across its effective area. Preferably the SLM is pixellated and each pixel is controlled, preferably independently, to control its interaction with radiation. Preferably the SLM has its regions or pixels controlled by the beam controller.

The SLM could be provided at or between the alignment element and a source of second wavelength radiation, or after the alignment element (in the path of an emitted beam). The output beam of second wavelength radiation may be generated from a single light source, or a few light sources. Alternatively there may be a large number (e.g. twenty or so, two or three hundred, or more) light sources (e.g. LEDs such as laser LEDs) which may form a pixellated light/second wavelength radiation output light source. This may be used to control the beam profile, with or without a SLM in the output optics.

The emitter may be adapted to emit third, or further, wavelength beams.

Preferably the device has a beam registering device adapted to interact with incident radiation of a first wavelength so as to have the incident radiation encounter the detector, and adapted to interact with the emitted radiation so as to cause the emitted radiation to follow substantially the same propagation path as the incident radiation once the emitted radiation has passed the beam registering device. The beam registering device preferably reflects or transmits at least part of an incident beam to the detector and reflects or transmits at least part of an emitted beam back along the path of the incident radiation. It will be appreciated that the beam combiner may comprise an inclined surface or member that is reflective to radiation of one of the first or second wavelengths and transmissive for the other (it need not split either beam). Alternatively the beam registering device may split one or both of the incident and emitted beams.

The central axis of the detector and of the emitter may be orientated at an angle to each other, preferably orthogonally. A focusing or collimating lens or lens assembly may be provided associated with the emitter and/or detector.

Signals preferably electrical, produced by the detector, or detector imager, may be passed substantially unprocessed to the emitter. This is fast, and cheap, and uses little or no computer processing power.

Emitted beam emphasising means may be provided. This may comprise a strobe adapted to cause the emitted beam to flash. Alternatively the device may be provided with a background sensor sensitive to radiation of the second wavelength, the background sensor being adapted to determine the background intensity of radiation of the second wavelength in the field of view of the device and to provide signals to an intensity controller adapted to control the intensity of the emitted beam at the second wavelength so as to ensure it is of a significantly higher intensity that the background intensity, thereby enabling the emitted beam to stand out on the scene (assuming that the scene has a surface to be illuminated). The background sensor may additionally or alternatively provide signals to an emitted beam wavelength selector which selects between more than one second wavelength of radiation (i.e. the second wavelength can be selected one of a plurality of different wavelengths) to ensure that the emitted beam has a second wavelength that is different from the predominant wavelength of the background scene. Thus the colour of the emitted beam may change depending upon the colour of the scene being illuminated so that the projected image stands out more. The device may have a plurality of colour sensors and the wavelength may select a chosen one of a predetermined plurality of wavelengths, choosing the one (or more than one) which has the greatest visual contrast with the scene. If red, green and blue light sources are provided then any visible band colour can be generated by appropriate mixing/combination.

The emphasising means may comprise a background sensor adapted to determine the predominant visible wavelength of radiation in the scene and to provide background wavelength signals to an emitted beam wavelength selector which is adapted to select one of a plurality of possible visible second wavelengths of radiation to ensure that the emitted beam has a second visible wavelength that is different from the predominant visible wavelength of the background scene.

The device is preferably hand-held and may comprise a torch. Alternatively the device may comprise an assembly mounted on a larger assembly, for example on a vehicle, or on a building, or lighting gantry. The device may be mounted on a helmet.

The device may include a sensor sensitive to radiation of the second wavelength, and a directional or imaging detector and directional or image projector as the emitter, and deselection control means being adapted to identify areas of the scene being observed that are the source of a significant amount of radiation of the second wavelength to the device and to deselect those regions for illumination by the emitter. In this way a vehicle travelling at night with its lights on does not get blinded by being illuminated by a beam of light from the device, because it is deselected as already being illuminated visible light.

The sensor sensitive to radiation of the second wavelength may comprise an imager, for example a camera.

In the preferred embodiment where infrared is sensed and visible light projected, the device (or assembly) may have both an infrared camera and a visible light camera.

Because the intention is to use the detected I.R. signals to control the output visible beam there is no need to image the I.R. image to high resolution since it will not be seen directly by the user. Depending upon whether the device will project out an image in visible light of the detected I.R. image or not, there may be no need to have an imaging I.R. sensor: just a directional sensor and/or a thermal source sensor may be enough.

The device may be adapted in use to illuminate a detected source of first wavelength radiation with second wavelength radiation (and possibly adjacent regions), or to illuminate regions adjacent to the source, but not the source itself.

The device may have a detecting imager with a plurality of pixels and an emitter adapted to project an image with substantially the same number of pixels.

According to another aspect the invention comprises a receiver/emitter device or assembly which collects incident radiation of a first wavelength and uses that radiation to control the emission of radiation of a second wavelength.

Preferably the first wavelength radiation controls at least one of (i) the direction of emission of emitted second wavelength information, or (ii) the profile of the emitted beam; or (iii) the timing of the emission of the second wavelength radiation, or any two of (i), (ii) or (iii), or all three of (i), (ii) and (iii). Preferably the device images the incident first wavelength radiation and projects back an equivalent image in radiation of the second wavelength.

According to another aspect the invention comprises a method of projecting radiation onto a scene comprising receiving radiation of a first wavelength and using the received radiation to control the projection of radiation of a second wavelength onto the scene.

In the most preferred embodiments the method comprises detecting infrared radiation and emitting visible light. Preferably the visible light is emitted in the same direction as that from which the infrared is received. Preferably an image or pattern is detected in infrared and a corresponding image or pattern in visible light is emitted. Preferably the visible image or pattern is superimposed upon the equivalent infrared image or pattern in the illuminated scene.

The method may comprise determining whether the infrared object that is to be illuminated with visible light is already illuminated with visible light, and if it is already illuminated the method may comprise not illuminating it with visible light after all.

The method may comprise illuminating a region adjacent an infrared object with visible light (the object itself may or may not be illuminated with visible light). The method may comprise providing a user with a hand-held torch to perform the illumination in visible light of infrared sources.

Signals may be sent substantially directly from the detector, substantially unprocessed, to drive or control the emitter. An imaging detector may provide signals to control the output of an imaging emitter. Both the emitted radiation and detected radiation may encounter alignment means which may comprise a common alignment member.

An output beam may be steered by beam steering means, which may comprise a reflector. Alternatively or additionally the beam steering means may comprise a pattern displayed on a SLM (reflective or transmissive SLM).

Incident or emitted radiation, or both, may be focused or collimated. Conventional optical bodies may be provided to do this. Alternatively or additionally patterns displayed on an SLM can act as lenses (e.g. Fresnel lenses). A combined pattern displayed on an SLM could perform the function of beam steering and focusing or collimation.

The output image may be formed by using a plurality of light sources.

The invention has applications in many areas, and indeed there may be separate inventions in deciding to use the invention in some of the these specific areas. For example the invention can be used in the medical field (e.g. to pick out in visible light on the patient themselves hot or cold (or both) areas); the field of security (an intruder may be followed by a beam of light, and possibly dazzled by it, whereas a chasing officer may have the beam of light not projected onto him, but insisted onto the path he must follow to meet up with an intruder—both serving to guide the officer and to help him see the ground/his surroundings); as an early warning system for electrical faults; in fire-fighting, possibly on a helmet-mounted system, possibly projecting a scene in visible light onto a "screen" of smoke; in lighting (e.g. street lighting or stage lighting/where lighting can follow a person automatically); and for example in vehicles to improve night driving by illuminating hot bodies with visible light rather than using an in-vehicle infrared display.

According to another aspect the invention comprises a method of reducing the size of an infrared imaging array in an effective device adapted to show a user the shape of a hot, or different temperatured, body, the method comprising using an infrared sensor to control the output of a visible band projector and illuminating the body with visible light.

Thus, no display screen is provided.

According to another aspect the invention comprises a method of imaging anatomical structures comprising using non-visible band radiation to generate image-controlling signals related to the structure of the anatomical structure of interest and using those signals to control the output of a visible band projector to project onto the person or animal's body an image in visible light of the structure.

According to another aspect the invention comprises the use of a first wavelength-to-second wavelength image converter in the production of an anatomical image for assistance in the diagnosis of a disease, disorder or problem.

According to another aspect the invention comprises an infrared image to visible band projector of an image equivalent to the infrared image in the detection of hot or cold regions in an observed scene.

According to another aspect the invention comprises a method of improving the safely of driving in the dark comprising mounting on a vehicle a visible light projector which identifies warm objects and illuminates them with visible light.

According to another aspect the invention comprises a method of reducing the light emitted by a series of street lights by controlling them to illuminate warm objects and their vicinity preferentially, and not to illuminate to the same extent regions where there are no detected warm objects.

Infrared scene projectors are known, but are quite different to the present invention. Infrared scene projectors are used to test the performance of I.R. camera systems and they project an I.R. beam into space and onto a surface (e.g. wall or screen) to simulate the infrared signature of an object that the I.R. camera system is to look for in use. The I.R. camera system can then be worked on and optimised to detect objects with a similar I.R. signatures. Such infrared scene projectors project infrared light to simulate the presence of hot things.

BRIEF DESCRIPTION OF THE DRAWINGS

Embodiments of the invention will now be described by way of example only, with reference to the accompanying drawings of which:

FIGS. 12A and 12B show street lighting incorporating the invention;

FIGS. 13A and 13B show person detector systems in accordance with the invention;

FIG. 14 illustrates the use of the invention to identify a burn area, or an area of poor circulation;

FIG. 15 illustrates the use of the invention to detect pre-catastrophic faults in electrical wiring systems;

FIG. 16 illustrates another helmet using another aspect of the invention; and

FIG. 17 illustrates a detail of some embodiments of the invention.

DETAILED DISCUSSION OF EMBODIMENTS

Figure 1:
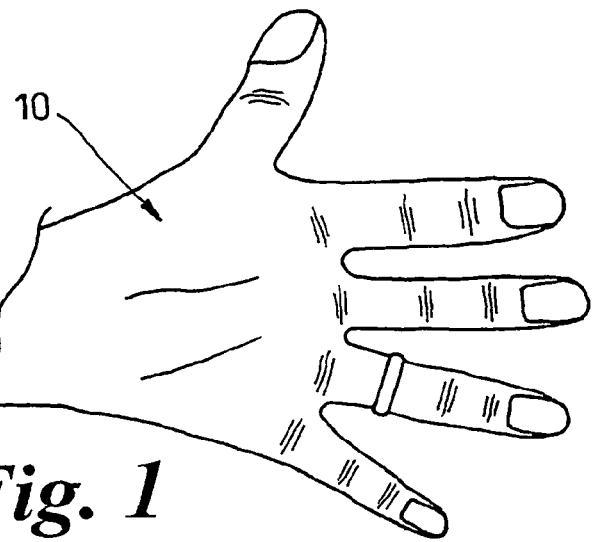
FIG. 1 shows a hand.

FIG. 1 shows a person's hand. It is difficult to see their veins. This can make it difficult to introduce a needle into a vein in the back of their hand.

Figure 2:
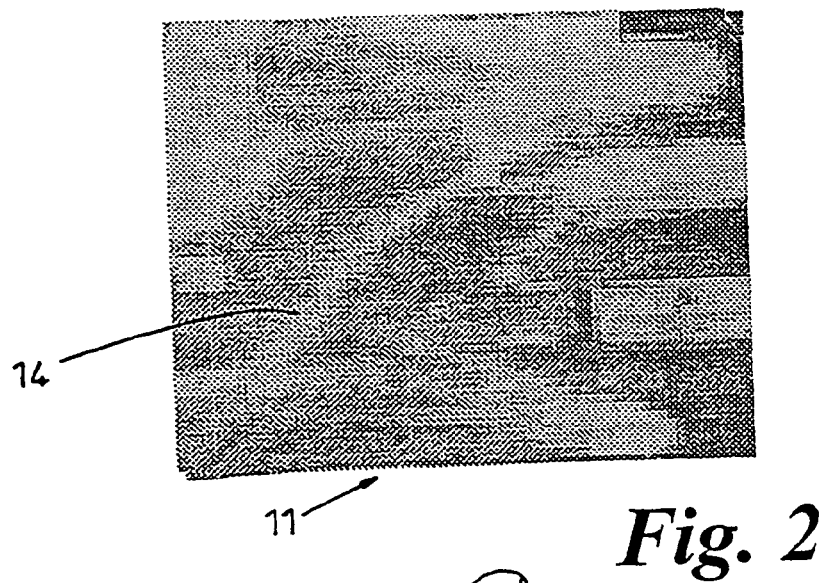
FIG. 2 show an infrared image of the hand.

FIG. 2 shows an infrared image 11 obtained by a thermal torch 12 of the hand 10. The veins, because they are warmer than the remainder of the back of the hand, show up as white/pale lines 14. It will be appreciated from what follows that the image 11 is not shown to the user of the torch 12 on a screen and may only exist within its torch as data/signals.

Figure 3:
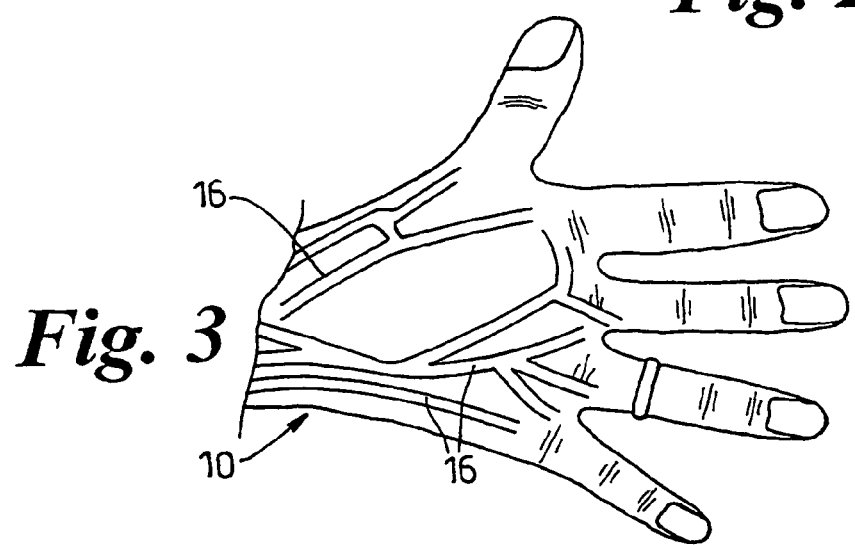
FIG. 3 shows an embodiment of the invention where a visible light image equivalent to the infrared image of FIG. 2 is projected in visible light onto the hand of FIG. 1.
Figure 4:
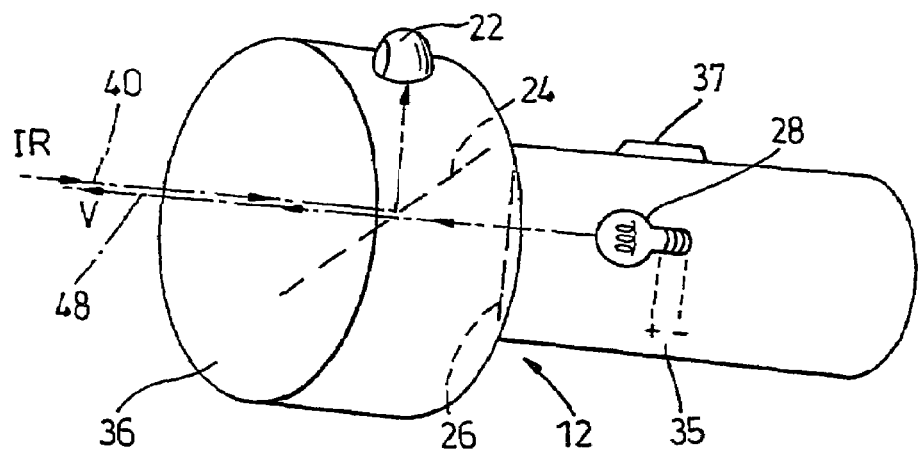
FIG. 4 shows schematically a thermal torch in accordance with the invention.
Figure 5:
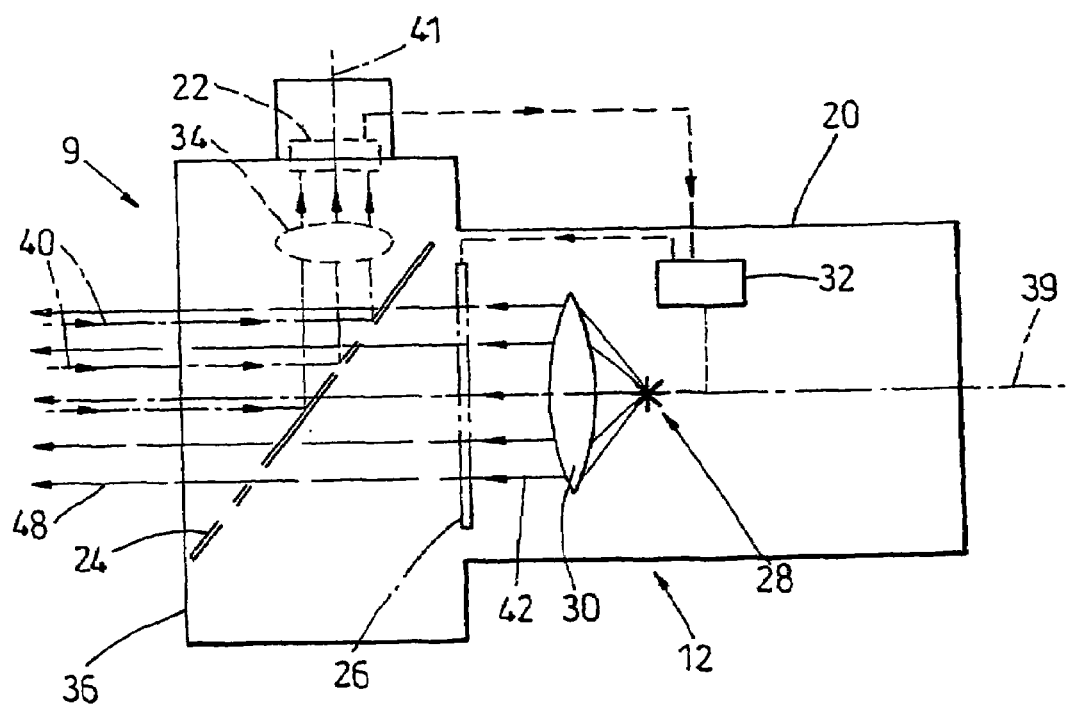
FIG. 5 shows a schematic cross-section of the torch in FIG. 4.

FIG. 3 shows the person hand 10 as seen by the user of a thermal torch 12 (shown in FIGS. 4 and 5). Lines 16 of white light are projected onto the hand 10 overlying the veins as detailed in the thermal image 11. The user can therefore take the torch 12, shine it on a patient's hand and see using their normal eyesight where the veins are because the torch picks them out in visible light. The torch could, of course, pick the veins out in blue, or red, or another non-white colour so that they stand out from the patients skin colour.

The torch 12 may have mechanisms to select an appropriate colour an/or intensity for the lines 16 so that they stand our clearly to the user. The torch may strobe or flash the lines 16.

The torch 12 itself is shown in FIGS. 4 and 5 and comprises a housing 20 surrounding an infrared imaging detector array 22, a selective transmitter/reflector 24, a beam patterner 26, a visible light source 28, collimating optics 30, and a controller 32. An infrared focusing lens 34 may be provided, or it may not. The device has an imaging aperture 9. A transparent (to both infrared and visible light) protective front sheet 36 is provided attached to the housing 20. An on/off switch 37 is provided, as is a battery 35. The imaging detector array 22 is a pixellated thermal sensor array, schematically shown in FIG. 17, having 64×64 pixels. This is usually considered to be too poor resolution to give good images. In another example the array has 32×32 pixels or 16×16 pixels, or 8×8, or 4×4, or 2×2 pixels. Each pixel, referenced 38, provides its own electrical signal to the controller 32. The array 22 is provided off-axis (off a central optical axis 39 of the torch).

The selective transmitter/reflector 24 is a plate inclined at about 45° to the central optical axis 39 of the torch 12. It reflects at least some (and perhaps substantially all) incident infrared radiation (referenced 40) up to the array 22. The central, line referenced 41 of the array 22 is substantially orthogonal to the central axis 39.

The beam patterner 26 comprises an LCD display having as many pixels 43 as the detector array 22 (in this example—in other examples it may have more or fewer pixels, possibly so that the number of pixels in one of the array 22 and patterner 26 is an integral multiple of the pixels in the other). The LCD patterner in the example of FIG. 5 is used in transmissive mode and is interposed between the light source 28 and the front surface 36 of the torch. In another example the LCD could be used in reflective mode. The pixels of the LCD display 26 are controlled by electrical signals from the controller 32.

As will be appreciated the positions of the LCD and light source and the infrared imager could be inverted. The pixels of beam patterner can be bigger or smaller than those of the I.R. imager or substantially the same size.

The light source 28 comprises an electric bulb capable of emitting substantially white light. In an alternative embodiment it may be a diode, or diode array, and may comprise a plurality of differently coloured light sources, e.g. red, green and blue diodes (or other light sources). The bulb is controlled by the controller 32. The collimating optics 30 comprises an aperture plate (not shown) and a glass or plastics convex lens spaced from the bulb 28 such that a substantially parallel beam 42 of white light is provided. The beam 42 passes through that beam patterner 26 and a pattern or profile is imposed onto the beam depending whether the pixels 41 are "dark" and absorb or reflect light, or whether they are clear and transmit light.

The detector array 22 refreshes itself, under control of the controller, at 50 Hz and the beam pattern refreshes itself, under control of the controller, at 50 Hz. Of course for a hand-held torch (or indeed other devices) the refresh rate could be much lower, for example 25 Hz, 10 Hz or even 5 Hz or lower. The refresh rate of the detector array need not be the same as that of the beam patterner.

It will be appreciated that the beam patterner comprises a spatial light modulator (SLM) and that other forms of SLM exist which could be suitable, for example non-pixellated SLMs and movable/micro mirror SLMs. Any SLM that can create a variable image in visible light could be used, as could other ways of creating a variable projected image (e.g. a scanning laser (no SLM), or an array of light outputters (e.g. diode array)).

The controller 32 comprises a printed circuit board which takes input signals from the pixels 38 and uses them to control output signals to the pixels 43. Little or no signal processing occurs. The device can be hardwired, but it may be convenient to use a micro-processor controller. Alternatively, the detected I.R. signals may be signal processed as part of creating drive signals for the beam patterner. As will be seen in FIG. 17 a detected image, referenced 44, in infrared is converted/mapped into an equivalent image, reference 46, in visible light, and projected onto the observed scene.

It will be noted that the optical arrangement of the visible light emitter system and the detected infrared detection system are bore-sighted: emitted light beam 48 is emitted from the torch in the direction from which came the infrared radiation 40.

The detector array 22 may be a thermal, infrared, digital camera.

Figure 6:
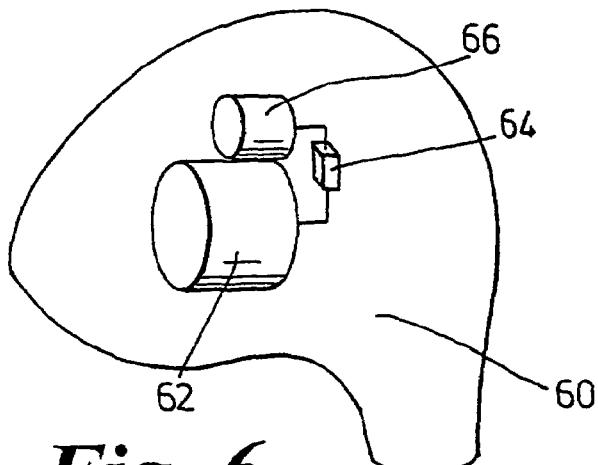
FIG. 6 shows a helmet provided with a thermal torch in accordance with the invention.

FIG. 6 shows a helmet 60 provided with a thermal torch unit 62 similar to that of FIGS. 4 and 5 and having a controller 64, and also provided with a visible light digital camera or sensor 66 which gathers light from the same direction as the thermal torch unit 62. The controller 64 uses signals from the visible light camera 66 to determine whether an object in the scene being observed by the thermal torch unit 62 is already illuminated with visible light or not. If it determines that the object is not illuminated (or is not illuminated above a threshold level) with visible light the controller 64 causes the torch unit 62 to illuminate the object with visible light if the object is warmer than the background (in other embodiments it does so if it is colder). If the controller 64 determines that a warm object is already illuminated with visible light it deselects it and does not cause the torch unit 62 to project visible light onto the object.

In this way the wearer of the helmet 60 can turn their head, with the torch unit 62 and visible light camera 64 pointing to their line of sight, and warm bodies (e.g. people, animals, hot parts of a person) will be illuminated with visible light unless they are themselves a light source/visibly bright. This avoids a user looking at a passing car or cyclist (which has its headlights on) and dazzling the driver or cyclist by shining visible light at them (because the car will be hot) and yet allows the user to look at, for example, escaping unilluminated pedestrians and have the thermal torch unit illuminate them. The user can then see, without using a separate display screen, where the pedestrian is. The user may have a battery pack, e.g. on the opposite side of the helmet to the camera 64 to act as a counterbalance.

Figure 7A:
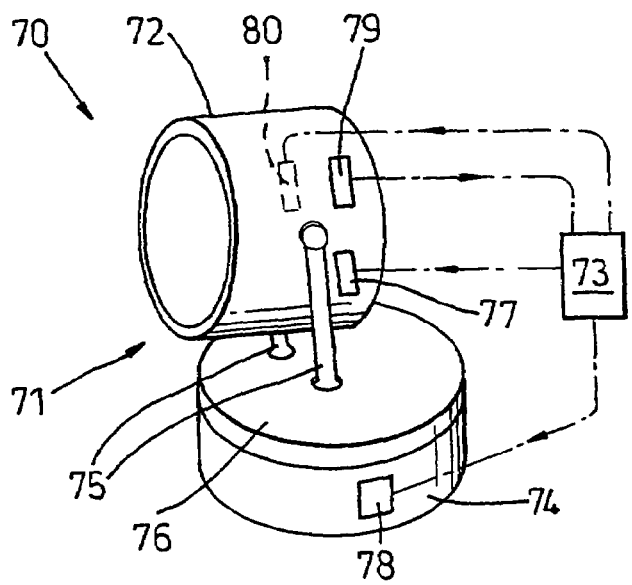
FIGS. 7A and 7B show stage lights in accordance with the invention.

FIG. 7A shows a floodlight or spotlight assembly 70 which comprises a thermal torch assembly 71 (similar to torch 12) having a body 72. A controller 73 for the assembly 70 is shown external to the housing of the torch assembly, but could of course be provided within the torch housing, or within a mounting base 74 upon which the torch assembly is mounted. The cylindrical body 72 of the torch assembly is pivotally mounted on arms 75 which are in turn mounted on an angularly movable carrier 76. An electric motor 77 controlled by the controller 73 controls the angular movement of the body 72 of the torch assembly relative to the arms 75. An electric motor 78 controlled by the controller 73 controls the angular movement of the carrier 76 relative to the base 74. The base 74 is attached (e.g. screwed) to a support. The body 72 can point at substantially all angles with a predetermined cone because of its gimbal mountings.

FIG. 7A shows an infrared sensor 79 which has only a few pixels. In this example, the device does not have a visible light beam patterner equivalent to the SLM 26 of FIGS. 4 and 5, but it could have one (and one is illustrated in dotted outline referenced 80).

The floodlight or spotlight assembly 70 can be used as a stage light or theatre light, or as an intruder/security light. It is conveniently mounted on a gantry, post or building (e.g. wall) but could be mounted on a vehicle such as a helicopter, boat, or car.

The controller receives signals representative a scene viewed in infrared from the crude 64×64 pixel array 79 and has software designed to lock onto a selected hot object and to cause the motors 77 and 78 to cause the optical axis of the body to follow the selected object around automatically. There may be a user input interface (e.g. connection from a PC) to enable the user to select one of a plurality of hot objects to track. Thus when used as a stage light the assembly 70 can follow an actor around automatically with an emitted beam of visible light.

The infrared detection is not used to image the actor, only to centre the visible light emitted by the assembly on the detected selected hot-spot. This means simple and cheap I.R. sensors can be used, which need not even be an array.

When it is desired simply to shine a spotlight on an object no beam profiling is necessary and no LCD beam profiler may be provided. The assembly (indeed, any embodiment of the invention) may have beam focusing means controlled by the controller which may automatically control the size of the projected area of the spotlight either to a fixed size or to a predetermined diameter which may change with time. One or more colour filters may be movable onto and out of the emitted beam to enable different colour beams to be emitted (this may also be applicable to any embodiment of the invention).

For some lighting effects, it may be desirable to pick out the shape of a hot (or cold) object and illuminate it, but substantially not illuminate things near to it with the spotlight (or alternatively do the opposite: illuminate things around an object but not the object itself). A beam profiler would then be provided.

It will be appreciated that in this embodiment, and indeed all other embodiments of the invention, it may be desirable to illuminate differentially objects that are colder than their scene surroundings. Thus "hotter" and "hot" can be read as something like "of significantly different temperatures (hotter or colder) than the surrounding scene viewed by the device".

Figure 7B:
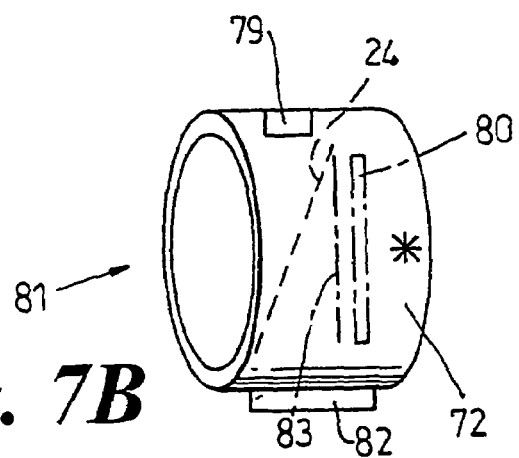

When used as an intruder/security light the assembly 70 works in very much the same way as discussed in relation to FIGS. 7A and 7B. In both its security application and stage light application it may be arranged not to emit visible light until a warm (or cold) body is in its field of view.

FIG. 7B shows a similar light unit, referenced 81, which has its body 72 mounted to a support 82; the body is not movable relative to the support.

Instead the visible light beam (and the direction from which infrared radiation is detected), is steered by internal components. A steering member 83 is controlled by the controller to steer the optics of the unit 81. The steering member 83 could be a physically movable/orientable optical element such as a mirror (e.g. concave mirror), or it could have no moving mechanical parts. For example a spatial light modulator displaying a pattern (e.g. of rings) can act as a zone plate/Fresnel lens and steer an effective optical axis. The controller could, of course, drive the steering pattern displayed on the SLM.

The light unit 71 or 81 could be used as a search and rescue spotlight, for example in a boat or airborne vehicle. It could automatically pick out a hot body and may be programmed to scan an area automatically and lock on to detected hot bodies.

Figure 8:
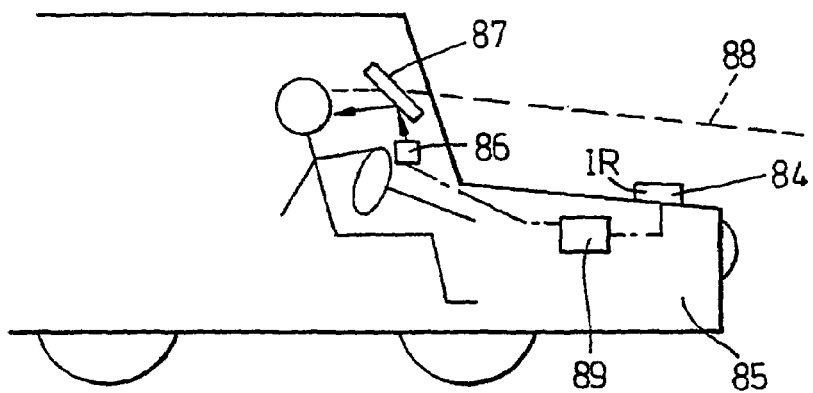
FIG. 8 shows a prior art infrared night driving system for a car, with a head-up display.

Another significant area of application for the invention is in vehicles, such as automobiles. FIG. 8 shows a prior art infrared night driving system which has an infrared camera 84 mounted on a car 85, a visible light projector 86 provided in the drivers area of the vehicle, a head-up display reflective panel 87 provided in a line of sight 88 of the driver, and a controller 89 which receives signals from the I.R. camera and controls the visible light output of the projector 86. The infrared camera has a high quality imaging detector array having, for example 512×512 pixels, and the projector 86 has a high quality imaging output having for example 512×512 pixels so as to generate on the head up display 87 a visible light representation of the whole I.R. scene viewed by the camera 84. Hot things will show up clearly to the driver. However, the driver may have a tendency to focus on the display 87 too much (the display may be only 10 cm×10 cm), creating a form of tunnel vision and effectively reducing the amount of windscreen they look out of. The head-up display mixes the 2-D low resolution infrared image with the high resolution normal 3-D view of the road and this can cause problems of misregistration of the two images as well as potential misinterpretation of the scene.

Figure 9A:
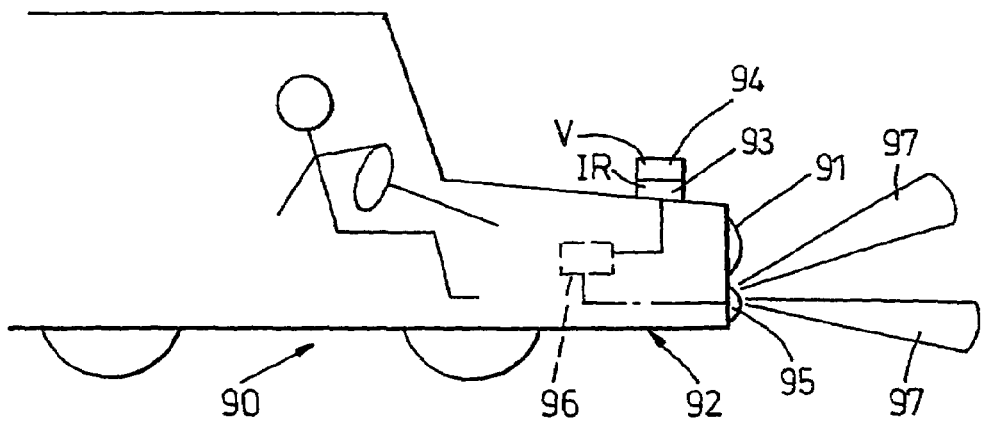
FIGS. 9A and 9B show schematically a car in accordance with the invention.
Figure 9B:
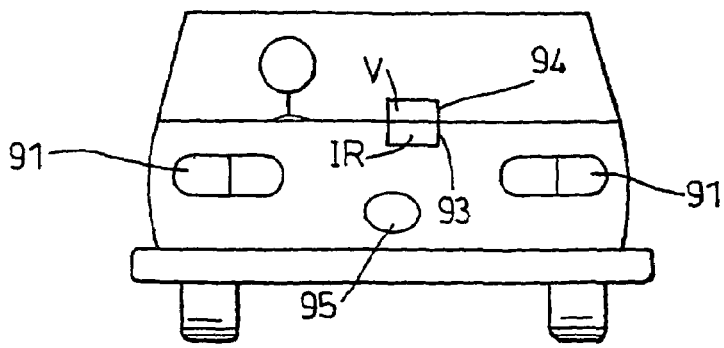

FIGS. 9A and 9B show a car 90 provided with the present invention. The car has headlights 91 and a night driving system 92 comprising an infrared camera 93, a visible light camera 94, an additional light 95, and a controller 96. The additional light 95 is steerable under the control of the controller 96 to direct its beam of visible light to wherever the controller directs it (within an allowable range of angles, e.g. 120°, or 160°, or even 180°, in the horizontal plane: it may be steerable in the vertical plane, or it may not).

The controller 96 receives signals from the infrared camera and uses the I.R. information to point the visible light beam, referenced 97, from the steerable light 95 at warm objects (which could be animals or people).

In this way, the driver looks through the full windscreen as they do for daytime driving: it is not a noticeably different experience for the driver, they just get warm things illuminated (in addition to illumination from their normal headlights). Moreover, there are fewer components intruding into the driver's space: no projector 86 and no head-up display 87.

A problem with the above is that other cars may appear as hot things to the infrared camera. It is not so bad to illuminate the rear of a vehicle that one is following (but even this may be undesirable), but it is not desirable to direct the beam 97 at oncoming vehicles since it may dazzle the drivers/riders. Visible light camera 94 is provided to avoid this. Camera 94 provides visible light scene information to the controller 96. If a hot body is detected the controller checks to see whether it is already bright enough in the visible camera before deciding whether to direct the beam 97 at it. If it is already visibly bright (e.g. an oncoming car with its headlights on) the controller de-selects it for attention and does not direct the beam 97 onto it.

Of course, there may be more than one hot body in the scene viewed by the I.R. camera 93. The controller could switch the beam 97 between two or more hot objects, possibly strobing them. Alternatively or additionally more than one steerable light 95 may be provided and they may be aimed at different objects.

Instead of, or in addition to, having an additional steerable light the vehicle may have its main headlights steerable, or the additional steerable light may be incorporated into a headlight assembly.

It will be appreciated that the beam(s) 97 will track a hot object as there is relative movement between the car and the object. When no hot object is in the field of view the beam 97 can be directed at the road ahead (e.g. as the normal headlights), or even switched off. It is preferred to keep the beam 97 on, but directed in an innocuous direction.

The system 92 may have pattern recognition software to recognise the back of a car in front of the driver (even at low light levels) and deselect it for illumination by the beam 97. Other means may identify the presence in front of the vehicle of another car with its exhaust hot, and deselecting it, may be provided. Further, the system 92 may comprise image processing software capable of identifying pedestrians and cyclists and select these as preferential objects for illumination.

Figure 10:
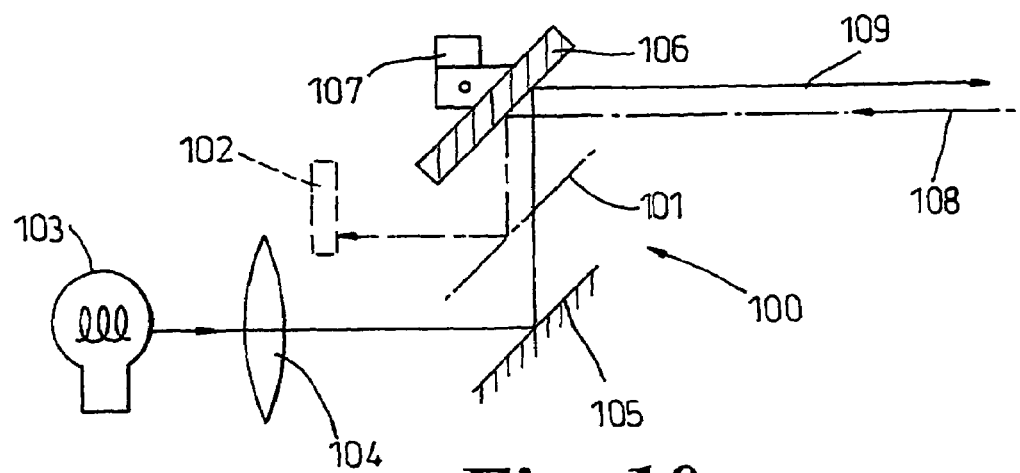
FIG. 10 shows a detail of a light of the car of FIGS. 9A and 9B.

FIG. 10 shows a steerable light unit 100 for a vehicle having an infrared and/or visible light reflector 101, an infrared and/or visible light detector 102, a light source 103, beam-forming optics 104, a fixed mirror 105, and a steerable mirror 106. Movement of the steerable mirror is controlled by a motor 107 under the control of a controller (e.g. controller 96). The mirror 106 can be moved very fast (fast enough to beam-steer effectively in a driving situation). The incoming radiation 108 (visible and/or infrared) is bore-sighted with the output visible radiation 109.

Figure 11:
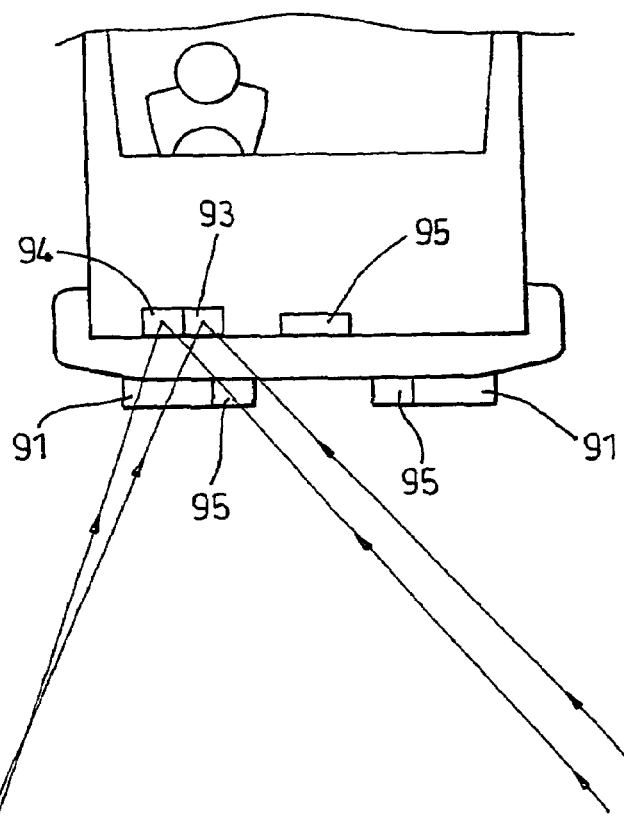
FIG. 11 shows another view of the car of FIGS. 9A and 9B.

FIG. 11 shows another embodiment of a night driving system similar to that of FIGS. 9A and 9B, but shows the visible sensor 94 and infrared sensor 93 side-by-side, with substantially overlapping fields of view.

The light unit 95 or 100 may have a beam profiler to profile the cross-sectional shape of the beam to match the shape of the detected I.R. image. It will be appreciated that the resolution of the profiling will be limited by the resolution of the I.R. imaging.

FIG. 12A shows a row of street lights 120, 121, 122 with light units 123 which have an infrared detector and a controller 124. The controller causes only those lights in the vicinity of a warm body to be illuminated. Thus, a row of street lights can be off, saving energy and reducing light pollution, until a pedestrian or vehicle comes within range. The controller 124 receives signals from different units 123 and using appropriate software can determined the direction of travel of a hot body and can cause those lights in front of the traveller to be illuminated (to a certain range) and all, or at least some, of those lights behind him to be turned off. As shown in FIG. 12A, a pedestrian is walking to the right and light 120 is off whilst lights 121 and 122 are on. This asymmetric light distribution around a hot body can save energy, especially if three or four or more lamps/Lights are on in front of the body and fewer, or one or none, behind the body.

FIG. 12B shows another street lighting system in which lamp posts have light units 120 as described with reference to FIG. 7A or 7B and a beam (wide angle divergent beam) of light follows a hot object as it moves.

FIG. 13A shows a light unit 130 substantially as described with reference to FIG. 7A or 7B. The unit 130 shines a circular beam of light at a warm object.

FIG. 13B shows a light unit 131 substantially as described with reference to FIG. 7A or 7B, but with a beam profiler to modulate the profile of the emitted beam. The unit 131 shines an annular beam 132 of light around a hot object. This allows a person (when they are the hot object) to see their immediate surrounding without being dazzled by the light beam.

FIG. 14 shows a use for the invention in the medical field. It shows a leg illuminated with visible light from a light unit having an infrared detector and profiled beam visible light emitter. A patch/area 140 of tissue is illuminated and differentiated to the user's normal vision by visible light. In one embodiment the area 140 is a cooler area of tissue, possibly indicating circulatory problems. In another embodiment the area of tissue is a hot area, possibly indicating a burned area of tissue.

It will be appreciated that it may be desirable to "greyscale" the projected visible light to differentiate between different temperature regions on an illuminated body. The different areas indicative of different temperatures may be illuminated by different colours of visible light (e.g. red, yellow, green, blue). The differentiation could be achieved by different light intensities for different temperature regions, or different regions being illuminated at different times, or a combination of differentiation techniques.

FIG. 15 shows another use for the invention. An area of wall 150 in a room is viewed with a device in accordance with the invention and a hot area 151 is illuminated by the device with visible light. In this example the hot area is an overheating fuse box, or section of electrical wiring, which may be a fire risk. Having it highlighted enables pre-emptive remedial action to be taken. The device could be portable, e.g. hand-held (i.e. be like torch 12), or it could be a fixed, permanently or periodically operating, monitor device. The device may have a beam profiler, in which case the profile 152 of the hot area can be shown, rather than just its general location (spot 151).

FIG. 16 shows a fireman's helmet 160 with a projector device 161 which detects an infrared image and projects an equivalent image back out in visible light. When the fireman is in thick smoke, referenced 162, the visible image is projected onto the smoke which effectively forms a projection screen. The fireman can therefore see, without a head-up display or other sight-impairing display, a visible image of the scene, despite the smoke.

FIG. 17 schematically illustrates the one-to-one mapping, in one embodiment, of information from pixels of an I.R. imaging array 22 to a visible light beam profiler 26.

It will be appreciated that an important feature of some embodiments is that a thermal camera is bore-sighted to a visible band projector all in the same unit (e.g. torch with an LC display). The thermal image collected by the camera is projected back onto the original scene using visible light. As a thermal camera is sensitive to heat, the torch illuminates only objects that are warm. So, as people are (typically) warmer than their surroundings, the projector will light them up in preference to the cooler background.

Applications, as previously discussed, include spotlight control for the stage (follow the players automatically), security lights (illuminate only intruder, not floodlight). The system could invert the projected image (i.e. "black hot") and used as a polo-mint light to guide people to where they might want to go but without dazzling them. Medical applications would allow identification of bad circulation, burns, etc., simply by shining the thermal torch at the patient.

At night, such a system could, for example, be built into a car, with a headlight used as the project or to illuminate warm objects—people, animals, cyclists, cars. It could be used in conjunction with a bore-sighted visible camera too, so that it did not illuminate already bright objects—e.g. oncoming cars. Light could be directed into the shadows without dazzling other road users. This would improve the ability to drive at night.

Instead of indirect view (as normal with a thermal imager), the thermal image is fused "in situ" with the original scene using visible light. This means that normal vision can be used (binocular, colour, high spatial resolution) with the projector beam simply highlighting areas of interest. This makes perception natural and the application (e.g. driving) safe and "user-friendly". An important advantage of many embodiments is that the spatial resolution requirements of the infrared system is kept very low compared with that required to generate a good quality image for inspection or driving. This makes a system concept economically viable.

It will also be appreciated that because the device refreshes its detected/projected images fast enough it can be moved around (e.g. hand shake, or on a vehicle) and yet the viewer may not really notice any significant change in the illumination of the scene object with visible light.

Once a person has a thermal torch similar to that of FIGS. 4 and 5 they can use it to check a wall/roof/windows/house for cold areas that require insulating; or inspect for hot spots in electrical systems, or use it for any of the uses discussed.

It will be appreciated that the infrared radiation of primary interest in the present invention is thermal infrared that is emitted by bodies naturally, without having to illuminate them with a source of infrared. This thermal infrared radiation often has a wavelength of around 10 μm. The wavelength of infrared radiation of active infrared sensors/imagers which emit a beam of infrared and look for reflected infrared is deliberately kept away from thermal IR wavelengths (to avoid thermal sources cluttering up their images), and is typically of the order of 1 μm. The present invention requires no I.R. illumination source: It uses an IR sourceless imaging device. It is a passive sensing technique without initial illumination of the observed scene with thermal infrared.

Some embodiments of the present invention are directed at low cost thermal imaging applications, and having an IR emitter can only increase the cost of a device.

Although passively detecting thermal IR and illuminating thermal sources with an equivalent pattern of visible light is the primary embodiment of the invention, the invention is not restricted to that. In a trivial, playing with words, example, it is possible to paint a patients body/hand with an ultra violet-sensitive paint which gives off visible light when illuminating with UV and to have a devise which detects a thermal IR pattern on the patients body/hand and superimposes a corresponding UV pattern on the body/hand, thereby causing a visible representation of the IR pattern to exist on the body/hand. Such a modification is, of course, within the scope of the present invention.

More widely, converting directional and intensity information of an observed scene from a non-visible information-carrier domain to a visible light mapping overlaid onto the real observed scene is the invention. For example the non-visible domain could be X-rays, near visible radiation, magnetic field mappings, atomic radiation mappings, radio mappings, radio interference highlighting, similarly, non-electromagnetic information domains can also be converted to a superimposed visible patterning, for example a pattern/image of an observed scene viewed in sound (acoustic to visible mapping), or ultrasound (e.g. shining light onto hairline cracks), or odours to visible light mappings, can all be envisaged. In each case an observer does not need to view a display screen, or wear special glasses: they can view the real world scene and see the visible pattern in it.

The invention claimed is:

1. A projector device comprising:
    a passive thermal infrared detector for detecting an intensity pattern of thermal infrared radiation emitted by objects in an observed scene and incident upon the device from a direction;
    an emitter adapted to emit a beam of radiation of visible light; and
    emitted beam control means for modulating the intensity of the emitted visible light beam to at least two intensity levels, said intensity levels based on the intensity pattern of said detected thermal infrared radiation, and for controlling the direction of said emitted visible light beam to selectively illuminate said objects of different temperature in the observed scene.

2. A device according to claim 1 in which the emitter has an emitted beam patterner, and in which the detector is adapted to detect the cross-sectional profile, or pattern, of said objects passively detected in an observed scene in infrared, and in which the emitter is adapted to emit an emitted beam with a variable cross-sectional profile which is modulated by the beam patterner to match the profile or pattern in infrared, and to superpose an equivalent visible light pattern over the infrared pattern in the observed scene.

3. A device according to claim 2 in which the beam patterner comprises a spatial light modulator (SLM) adapted to control an image emitted by the emitter.

4. A device according to claim 3 in which the spatial light modulator is provided at or between an alignment element adapted to align an emitted visible light image with a detected thermal infrared image and a source of visible light.

5. A device according to claim 1 in which an optical alignment element is provided to register the emitted beam with said objects, the alignment element being at least partially reflective to radiation of one of the thermal infrared and visible light, and at least partially transmissive to radiation of the other of the thermal infrared and visible light.

6. A device according to claim 5 in which the alignment element comprises a beam splitter.

7. A device according to claim 1 comprising a hand-held torch.

8. A device according to claim 1 in which signals produced by the detector are passed substantially unprocessed to the emitter.

9. A device according to claim 1 which has a sensor sensitive to visible light, and a directional or image projector as the emitter, and deselection control means being adapted to identify areas of the scene being observed by said sensor that are the source of a significant amount of radiation of visible light to the device, and being adapted to deselect those regions for illumination by the visible light emitter.

10. A device according to claim 1 which has said passive thermal infrared detector with a plurality of pixels and said emitter adapted to project an image with substantially the same number of pixels.

11. A method of visibly representing a thermal mapping of an observed scene comprising the steps of:
    receiving thermal infrared radiation of a first wavelength from said observed scene; and
    using the received infrared radiation to control the projection of visible light of at least two different intensities onto the observed scene, said intensity of light representing the intensity of said received thermal infrared radiation, the visible light being projected in a visible light pattern onto the observed scene that mirrors and overlays the thermal infrared map of the observed scene.

12. A method according to claim 11 comprising providing a user with a hand-held torch to project the visible light pattern onto the observed scene.

13. A method of improving the safely of driving in the dark comprising mounting on a vehicle a visible light projector which operates in accordance with claim 11 and illuminating thermal objects in an observed scene with visible light.

* * * * *